US008815261B2

(12) United States Patent
Hanma (10) Patent No.: US 8,815,261 B2
(45) Date of Patent: Aug. 26, 2014

(54) COMPOSITION FOR EXTERNAL APPLICATION COMPRISING ARIPIPRAZOLE AND ORGANIC ACID AS ACTIVE INGREDIENTS

(75) Inventor: Noritaka Hanma, Wakayama (JP)

(73) Assignee: MEDRx Co., Ltd., Higashikagawa (JP)

( * ) Notice: Subject to any disclaimer, the term of this patent is extended or adjusted under 35 U.S.C. 154(b) by 0 days.

(21) Appl. No.: 13/378,615

(22) PCT Filed: Jun. 17, 2010

(86) PCT No.: PCT/JP2010/004066
§ 371 (c)(1),
(2), (4) Date: Mar. 1, 2012

(87) PCT Pub. No.: WO2010/146872
PCT Pub. Date: Dec. 23, 2010

(65) Prior Publication Data
US 2012/0184563 A1    Jul. 19, 2012

(30) Foreign Application Priority Data

Jun. 19, 2009    (JP) .................................. 2009-146414

(51) Int. Cl.
| A61K 9/00 | (2006.01) |
| A61F 13/00 | (2006.01) |
| A61K 9/70 | (2006.01) |
| A61K 38/00 | (2006.01) |
| A61P 25/18 | (2006.01) |
| A01N 43/42 | (2006.01) |
| A61K 31/47 | (2006.01) |
| A61K 31/496 | (2006.01) |
| A61K 47/12 | (2006.01) |

(52) U.S. Cl.
CPC ............. *A61K 31/496* (2013.01); *A61K 9/0014* (2013.01); *A61K 47/12* (2013.01)
USPC ........... 424/400; 424/449; 514/17.5; 514/314

(58) Field of Classification Search
CPC .... A61K 31/496; A61K 47/12; A61K 9/0014
See application file for complete search history.

(56) References Cited

U.S. PATENT DOCUMENTS

| 5,006,528 | A | 4/1991 | Oshiro et al. |
| 6,620,429 | B1 | 9/2003 | Muller |
| 6,977,257 | B2* | 12/2005 | Parab et al. ............... 514/253.07 |
| 2002/0193438 | A1* | 12/2002 | Parab et al. .................... 514/557 |
| 2004/0170672 | A1* | 9/2004 | Selzer .......................... 424/449 |
| 2006/0110434 | A1 | 5/2006 | Yamaguchi et al. |
| 2008/0287677 | A1* | 11/2008 | Ludescher et al. ............ 544/363 |
| 2009/0004255 | A1 | 1/2009 | Uchida et al. |
| 2009/0169605 | A1* | 7/2009 | Maeda et al. .................. 424/448 |

FOREIGN PATENT DOCUMENTS

| EP | 0 367 141 A2 | 5/1990 |
| EP | 1 661 560 A1 | 5/2006 |
| JP | 2608788 B2 | 2/1997 |
| JP | 2002-509874 A | 4/2002 |
| JP | 2004-529891 A | 9/2004 |
| JP | 2006-169238 A | 6/2006 |
| JP | 2007-217313 A | 8/2007 |
| WO | WO 2007094385 A1 * | 8/2007 |
| WO | WO 2007/142295 A1 | 12/2007 |
| WO | WO 2007142295 A1 * | 12/2007 |
| WO | WO 2008/038003 A2 | 4/2008 |

OTHER PUBLICATIONS

Otsuka Pharmaceutical Co., Ltd., ABILIFY™ Package Insert (Jan. 2009).
Japanese Patent Office, International Search Report in International Patent Application No. PCT/JP2010/004066 (Jul. 20, 2010).

* cited by examiner

Primary Examiner — Brian-Yong Kwon
Assistant Examiner — Mark V Stevens
(74) Attorney, Agent, or Firm — Leydig, Voit & Mayer, Ltd.

(57) ABSTRACT

[Summary] An external preparation formulation superior in the transdermal absorbability has been desired as a new administration route of aripiprazole. Transdermal absorption of aripiprazole has been enabled for the first time by appropriately combining aripiprazole and an organic acid (particularly fatty acid with low lipophilicity). That is, it has been found that more superior transdermal absorbability can be achieved by forming a salt by using a compound showing lipophilicity within the range of −1.5-2, such as fatty acid and the like. It has been further found that the transdermal absorbability is remarkable improved by appropriately selecting the solvent composition. As a result, since a new dosage form of aripiprazole other than oral preparation has been developed, a new transdermal absorption preparation of aripiprazole can be provided.

10 Claims, 5 Drawing Sheets

COMPOSITION FOR EXTERNAL APPLICATION COMPRISING ARIPIPRAZOLE AND ORGANIC ACID AS ACTIVE INGREDIENTS

TECHNICAL FIELD

The present invention relates to a transdermal absorption type preparation containing aripiprazole known as an atypical antipsychotic agent and an organic acid. More specifically, the present invention relates to a preparation with good transdermal absorbability, which is obtained by adding an equimolar amount or more of an organic acid to aripiprazole.

BACKGROUND ART

Aripiprazole, i.e., 7-{4-[4-(2,3-dichlorophenyl)-1-piperazinyl]butoxy}-3,4-dihydrocarbostyryl or 7-{4-[4-(2,3-dichlorophenyl)-1-piperazinyl]butoxy}-3,4-dihydro-2(1H)-quinolinone, is an atypical antipsychotic agent useful for the treatment of schizophrenia (patent document 1).

Schizophrenia is a mental disease of a general type, which is characterized by delusion, hallucination and complete withdrawal from others. The sign of schizophrenia generally occurs between age 16 to 25, and schizophrenia is developed in one out of one hundred in the world. Schizophrenia is more often seen than Alzheimer's disease, multiple sclerosis, insulin dependent diabetes and muscular dystrophy. It is known that early diagnosis and treatment can markedly improve recovery and outcome, and further, a therapeutic intervention at an early stage can avoid costly hospitalization, and the like.

Generally, the starting daily dose of aripiprazole is 6-12 mg, and the daily maintenance dose is 6-24 mg, for an adult, and is orally administered in one or two portions a day (non-patent document 1). In addition, aripiprazole has a long half-life in blood of about 65 hr in healthy adults, and is an extremely superior medicament that is not easily influenced by diet.

Therefore, the development of a new administration method of aripiprazole has been tried, and a transdermal treatment absorption system (TTS) in the form of a plaster has been tried in addition to the oral administration route (patent document 2). However, specific effect is not at all described, and the characteristic of a transdermal absorption preparation is not clear.

While a transdermal absorption preparation containing a basic drug including aripiprazole and a copolymer containing polyvinylpyrrolidone as a main component is referred to, no specific Example is given and only risperidone is described (patent document 3).

When risperidone is used as a basic drug, an organic acid is added as a melting point lowering agent, and a superior amount of the organic acid to be used is described to be not less than the equimolar of risperidone (for example, 2- to 3-fold molar amount) (patent document 4).

However, a specific combination and an effect of aripiprazole and an organic acid are not considered at all. In addition, the transdermal absorbability derived from an organic acid salt of aripiprazole is not known at all.

DOCUMENT LIST

Patent Documents patent document 1: JP-B-2608788
patent document 2: National Publication of International Patent Application No. 2004-529891
patent document 3: JP-A-2007-217313
patent document 4: JP-A-2006-169238

Non-Patent Document non-patent document 1: Abilify Package Insert

SUMMARY OF THE INVENTION

Problems to be Solved by the Invention

The present invention aims to provide a transdermal absorption preparation containing aripiprazole and an organic acid, which shows good transdermal absorbability. Furthermore, the present invention aims to provide an external preparation composition containing an organic acid salt of aripiprazole, which shows good transdermal absorbability.

Means of Solving the Problems

The present inventors have added an equimolar amount of an organic acid to aripiprazole to form an organic acid salt of aripiprazole in the system, and studied the correlation between lipophilicity of the salt (since aripiprazole is fixed, logP of the organic acid is used instead) and transdermal absorbability of aripiprazole. As a result, it has been found that a transdermal absorption preparation having good transdermal absorbability can be produced by producing a salt with an organic acid having a logP within the range of −1.5 to 2.5 or an equilibrium mixture thereof. In the case of a monocarboxylic acid, for example, it has been found that a more preferable transdermal absorption preparation having good transdermal absorbability can be produced by producing a salt with a carboxylic acid having a logP within the range of −1.5 to 0 or an equilibrium mixture thereof. Furthermore, when a dicarboxylic acid is used, a more preferable transdermal absorption preparation can be produced by using a dicarboxylic acid having a logP within the range of −0.2 to 2.5. Moreover, when an aromatic carboxylic acid or a sulfonic acid derivative having a logP within the range of −0.7 to 2.5 is used, a more referable transdermal absorption preparation is obtained. Particularly, it has been found from the comparison of monocarboxylic acid, dicarboxylic acid salt, aromatic carboxylic acid salt and sulfonate that a monocarboxylic acid salt shows much better transdermal absorbability.

While aripiprazole is a compound having extremely good crystallinity, it has been further found that those organic acid salts of aripiprazole in non-aqueous transdermal absorption preparations with high concentration do not allow precipitation of aripiprazole crystals, and afford transdermal absorption preparations having high preservation stability. In addition, an organic solvent composition preferable for an organic acid salt of aripiprazole could be found. As a result, an external preparation composition can be easily produced by dissolving an organic acid salt of aripiprazole, and further, the transdermal absorbability of aripiprazole could be improved.

By increasing the amount of an organic acid as an additive of an external preparation composition, the equilibrium of salt formation in the preparation system can be directed toward salt. As a result, transdermal absorbability of aripiprazole can be further improved. Based on these results, the present inventors have completed the present invention.

Accordingly, the gist of the present invention is as follows.
(1) A transdermal absorption preparation comprising an organic acid salt of aripiprazole in the preparation system, wherein the organic acid is aromatic sulfonic acid, aliphatic sulfonic acid, aromatic carboxylic acid or aliphatic carboxylic acid, and the content of the organic acid is 0.5- to 5-fold molar amount relative to aripiprazole as 1.

(2) The transdermal absorption preparation of the above-mentioned (1), wherein the organic acid is aromatic carboxylic acid or aliphatic carboxylic acid.

(3) The transdermal absorption preparation of the above-mentioned (2), wherein the aliphatic carboxylic acid is substituted aliphatic monocarboxylic acid containing one or more hydroxyl groups and/or ketone groups as substituent(s).

(4) The transdermal absorption preparation of the above-mentioned (3), wherein the substituted aliphatic monocarboxylic acid is selected from lactic acid, glycolic acid and levulinic acid.

(5) The transdermal absorption preparation of the above-mentioned (2), wherein the aromatic carboxylic acid is benzoic acid or salicylic acid.

(6) The transdermal absorption preparation of any of the above-mentioned (1)-(5), comprising at least one selected from an ester solvent, an alcohol solvent and an amide solvent.

(7) The transdermal absorption preparation of the above-mentioned (6), wherein the ester solvent is at least one selected from isopropyl myristate, diethyl sebacate, medium-chain triglyceride and propylene carbonate.

(8) The transdermal absorption preparation of the above-mentioned (6) or (7), wherein the alcohol solvent is at least one selected from propylene glycol, 2-propanol, 1,3-butanediol, ethylene glycol and polyethylene glycol.

(9) The transdermal absorption preparation of any of the above-mentioned (6)-(8), wherein the amide solvent is at least one selected from N,N-dimethylformamide, N,N-dimethylacetamide and N-methyl-2-pyrrolidone.

(10) The transdermal absorption preparation of any of the above-mentioned (6)-(9), comprising both an ester solvent and an amide solvent.

(11) The transdermal absorption preparation of any of the above-mentioned (6)-(10), wherein the amide solvent is N-methyl-2-pyrrolidone.

(12) The transdermal absorption preparation of any of the above-mentioned (6)-(11), wherein the ester solvent and the amide solvent are contained at 1:1-1:4.

(13) The transdermal absorption preparation of any of the above-mentioned (1)-(12), wherein the organic acid and aripiprazole form an equimolar salt.

(14) The transdermal absorption preparation of any of the above-mentioned (1)-(13), which is a non-aqueous transdermal absorption preparation.

(15) A transdermal absorption preparation having good transdermal absorbability, comprising an organic acid salt of aripiprazole in the preparation system, wherein the organic acid has a logP of −1.5 to 2.5.

(16) The transdermal absorption preparation of the above-mentioned (15), wherein the logP of the organic acid is −1.5 to 0.

(17) The transdermal absorption preparation of the above-mentioned (15), wherein the organic acid is selected from glycolic acid, methoxyacetic acid, lactic acid and levulinic acid.

(18) The transdermal absorption preparation of any of the above-mentioned (15)-(17), comprising at least one selected from an ester solvent, an alcohol solvent and an amide solvent.

(19) The transdermal absorption preparation of the above-mentioned (18), wherein the ester solvent is at least one selected from isopropyl myristate, diethyl sebacate, medium-chain triglyceride and propylene carbonate.

(20) The transdermal absorption preparation of the above-mentioned (18) or (19), wherein the alcohol solvent is at least one selected from propylene glycol, 2-propanol, 1,3-butanediol, ethylene glycol and polyethylene glycol.

(21) The transdermal absorption preparation of any of the above-mentioned (18)-(21), wherein the amide solvent is at least one selected from N,N-dimethylformamide, N,N-dimethylacetamide and N-methyl-2-pyrrolidone.

(22) The transdermal absorption preparation of any of the above-mentioned (18)-(21), comprising both the ester solvent and the amide solvent.

(23) The transdermal absorption preparation of any of the above-mentioned (18)-(22), wherein the amide solvent is N-methyl-2-pyrrolidone.

(24) The transdermal absorption preparation of any of the above-mentioned (18)-(23), wherein the ester solvent and the amide solvent are contained at 1:1-1:4.

(25) The transdermal absorption preparation of any of the above-mentioned (15)-(24), wherein the organic acid is contained in a 0.5- to 5-fold molar amount relative to aripiprazole as 1.

(26) The transdermal absorption preparation of any of the above-mentioned (15)-(25), wherein the organic acid and aripiprazole form an equimolar salt.

(27) The transdermal absorption preparation of any of the above-mentioned (1)-(13), which is a non-aqueous transdermal absorption preparation.

(28) An equimolar salt of aripiprazole with an organic acid selected from lactic acid, glycolic acid and levulinic acid.

(29) A method of producing a transdermal absorption preparation with good transdermal absorbability, which comprises the following steps including formation of an organic acid salt of aripiprazole in the preparation system, a) forming an organic acid salt of aripiprazole by selecting a compound having a logP of −1.5 to 2.5 as an organic acid, and adding a 0.5- to 5-fold molar amount of the organic acid relative to aripiprazole, b) diluting the above-mentioned organic acid salt with at least one selected from an ester solvent, an alcohol solvent and an amide solvent, and c) dispersing the above-mentioned diluted solution in a base of an external preparation.

(30) The production method of the above-mentioned (29), wherein the organic acid is selected from glycolic acid, methoxyacetic acid, lactic acid and levulinic acid.

(31) The production method of the above-mentioned (29) or (30), wherein the ester solvent is at least one selected from isopropyl myristate, diethyl sebacate and medium-chain triglyceride.

(32) The production method of any of the above-mentioned (29)-(31), wherein the alcohol solvent is at least one selected from 2-propanol, ethylene glycol, propylene glycol and 1,3-butanediol.

(33) The production method of any of the above-mentioned (29)-(32), wherein the amide solvent is at least one selected from N,N-dimethylformamide, N,N-dimethylacetamide and N-methyl-2-pyrrolidone.

(34) The production method of the above-mentioned (33), wherein the amide solvent is N-methyl-2-pyrrolidone.

(35) The production method of any of the above-mentioned (29)-(34), wherein the ester solvent and the amide solvent are contained at 1:1-1:4.

(36) The production method of any of the above-mentioned (29)-(35), wherein the organic acid is contained in a 0.5- to 5-fold molar amount relative to aripiprazole as 1.

(37) The production method of any of the above-mentioned (29)-(36), wherein the organic acid and aripiprazole form an equimolar salt.

(38) The production method of any of the above-mentioned (29)-(37), which is a non-aqueous transdermal absorption preparation.

(39) A method of producing a transdermal absorption preparation with good transdermal absorbability, which comprises the following steps including formation of an organic acid salt of aripiprazole in the preparation system, a) forming an organic acid salt of aripiprazole by using aromatic carboxylic acid or aliphatic carboxylic acid as an organic acid, and adding a 0.5- to 5-fold molar amount of the organic acid to aripiprazole as 1, b) diluting the above-mentioned organic acid salt with at least one selected from an ester solvent, an alcohol solvent and an amide solvent, and c) dispersing the above-mentioned diluted solution in a base of an external preparation.

(40) The production method of the above-mentioned (39), wherein the aliphatic carboxylic acid is substituted aliphatic monocarboxylic acid containing one or more hydroxyl groups and/or ketone groups as substituent(s).

(41) The production method of the above-mentioned (40), wherein the substituted aliphatic carboxylic acid is selected from lactic acid, glycolic acid and levulinic acid.

(42) The production method of the above-mentioned (39), wherein the aromatic carboxylic acid is benzoic acid or salicylic acid.

(43) The production method of any of the above-mentioned (39)-(42), wherein the ester solvent is at least one selected from isopropyl myristate, diethyl sebacate, medium-chain triglyceride and propylene carbonate.

(44) The production method of any of the above-mentioned (39)-(43), wherein the alcohol solvent is at least one selected from propylene glycol, 2-propanol, 1,3-butanediol, ethylene glycol and polyethylene glycol.

(45) The production method of any of the above-mentioned (39)-(44), wherein the amide solvent is N-methyl-2-pyrrolidone.

(46) The production method of any of the above-mentioned (39)-(45), wherein the ester solvent and the amide solvent are contained at 1:1-1:4.

(47) The production method of any of the above-mentioned (39)-(46), wherein the organic acid and aripiprazole form an equimolar salt.

(48) The transdermal absorption preparation of any of the above-mentioned (39)-(47), which is a non-aqueous transdermal absorption preparation.

Effect of the Invention

The transdermal absorption preparation of the present invention contains a salt of aripiprazole (logP value: 4.6) and an organic acid (logP value: −1.5 to 2.5) or an equilibrium mixture thereof. Particularly, a transdermal absorption preparation with good transdermal absorbability and good stability, free of crystallization of aripiprazole even at high concentrations, and unachievable with aripiprazole alone, can be produced in the present invention by using a salt with aliphatic monocarboxylic acid substituted by a substituent such as lactic acid, glycolic acid and the like as an organic acid. As a result, a non-aqueous transdermal absorption preparation such as tapes can be practically produced with regard to aripiprazole.

Furthermore, since the transdermal absorbability of aripiprazole can be improved further, depending on the selection of the solvent composition, a transdermal absorption preparation of aripiprazole can be commercialized.

DESCRIPTION OF EMBODIMENTS

First Embodiment of the Present Invention

The first embodiment of the present invention is an invention relating to a transdermal absorption preparation containing aripiprazole organic acid salt formed in preparation system by aripiprazole and an organic acid.

The "aripiprazole" referred to in the present invention means 7-{4-[4-(2,3-dichlorophenyl)-1-piperazinyl]butoxy}-3,4-dihydrocarbostyryl (7-{4-[4-(2,3-dichlorophenyl)-1-piperazinyl]butoxy}-3,4-dihydro-2(1H)-quinolinone).

The "organic acid" referred to in the present invention means aliphatic monocarboxylic acid, aliphatic dicarboxylic acid, aromatic carboxylic acid, organic sulfonic acid and the like. Examples of the aliphatic monocarboxylic acid include short chain fatty acid having a carbon number of 2-7 such as acetic acid, butyric acid, hexanoic acid, cyclohexanecarboxylic acid and the like, middle chain fatty acid having a carbon number of 8-11 such as octanoic acid, decanoic acid and the like, long chain fatty acid having a carbon number of 12 or more such as myristic acid, stearic acid, isostearic acid, oleic acid and the like, short chain fatty acid substituted by a hydroxyl group, an alkoxy group or an acyl group such as glycolic acid, lactic acid, methoxyacetic acid, mandelic acid, levulinic acid, 3-hydroxybutyric acid and the like, and the like. Examples of the aliphatic dicarboxylic acid include sebacic acid, adipic acid, malic acid, maleic acid, fumaric acid and the like.

Examples of the aromatic carboxylic acid include substituted or unsubstituted aromatic carboxylic acid such as benzoic acid, p-hydroxybenzoic acid, salicylic acid, acetylsalicylic acid, cinnamic acid and the like. Examples of the organic sulfonic acid include alkylsulfonic acid such as methanesulfonic acid, ethanesulfonic acid, methyl sulfonic acid and the like, aromatic sulfonic acid such as benzenesulfonic acid, toluenesulfonic acid, dodecylbenzenesulfonic acid and the like.

Preferable examples of the organic acid include those having a logP value of −1.5 to 2.5, preferably −1.5 to 0, as aliphatic monocarboxylic acid. Examples thereof include short chain fatty acid substituted by a hydroxyl group, an alkoxy group, or an acyl group such as glycolic acid, lactic acid, methoxyacetic acid, 3-hydroxybutyric acid, mandelic acid, levulinic acid and the like, benzenecarboxylic acid such as benzoic acid, P-hydroxybenzoic acid, salicylic acid, acetylsalicylic acid and the like. More preferable examples of the aliphatic monocarboxylic acid include lactic acid, methoxyacetic acid, and glycolic acid wherein the logP value is −1.1 to −0.7.

Examples of the aliphatic dicarboxylic acid include substituted or unsubstituted aliphatic dicarboxylic acid such as adipic acid and sebacic acid, wherein the logP value is within the range of −0.2 to 2.5. More preferred is aliphatic dicarboxylic acid within the range of 0 to 2.5.

Examples of the aromatic carboxylic acid include those having a logP value of 1.5 to 2.5, such as benzoic acid and salicylic acid. More preferred are benzoic acid and salicylic acid.

Examples of the organic sulfonic acid include those having a logP value of −0.5 to 1.

Figure 3:
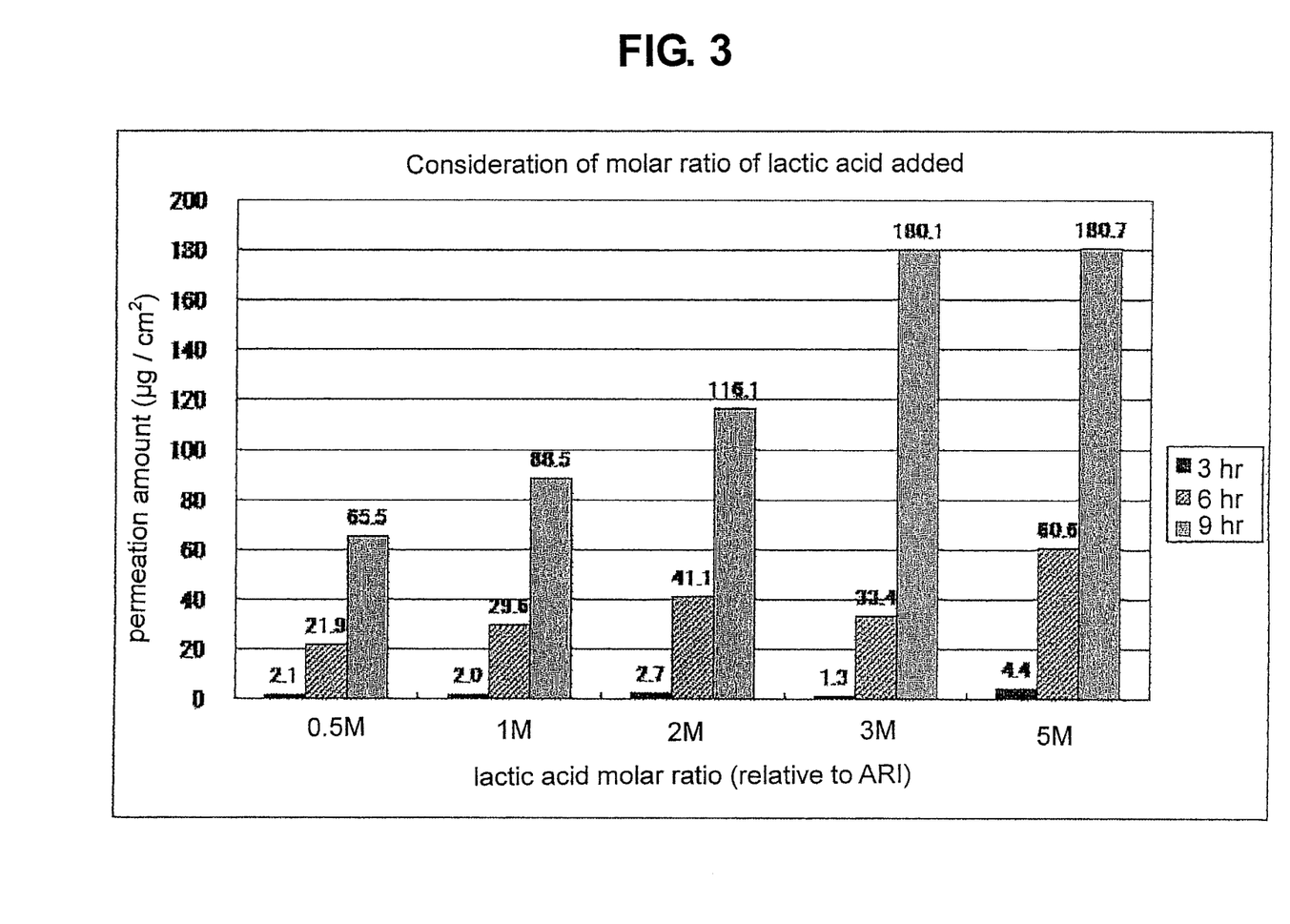
FIG. 3 shows the results of an in vitro transdermal absorbability test of the effect of addition of lactic acid to aripiprazole.

The amount of the organic acid to be added needs to be not less than 0.5-fold molar amount relative to aripiprazole as 1, so as to form an effective amount of an organic acid salt of aripiprazole in a solution. When an organic acid is added in excess, the dissociation equilibrium of the salt tilts to the salt, and therefore, when not less than 3-fold molar amount of an organic acid is present, the transdermal absorbability reaches the upper limit as shown in FIG. 3. Thus, a 5-fold molar amount of an organic acid is sufficient. Furthermore, the amount of an organic acid to be added is preferably not less than an equimolar amount and not more than 3-fold molar amount.

The "aripiprazole organic acid salt formed in the preparation system" in the present invention means that a preparation contains a salt formed by a reaction of aripiprazole with an organic acid, or an equilibrium mixture of aripiprazole and an organic acid. Particularly "formed in the preparation" means that a salt or an equilibrium mixture of aripiprazole and organic acid is formed in an organic acid or a solvent, and diluted or dispersed by mixing with a base of a dermal preparation.

The "transdermal absorption preparation" in the present invention refers to liquid, ointment, cream, patch and the like. The patch means poultice and plaster (tapes).

The transdermal absorption preparation of the present invention may contain a solvent suitable for forming a salt, so as to form a salt of aripiprazole in the preparation system. As this solvent, an ester solvent, an alcohol solvent and an amide solvent can be preferably used. Depending on the dosage form thereof, moreover, an additive known to and generally used by those of ordinary skill in the art can be appropriately added to this solvent. Examples of such additive include transdermal absorption promoter, base, surfactant, suspending agent, thickener, inorganic particle, stabilizer, buffering agent, pH adjuster, colorant, flavor and the like.

The "non-aqueous" in the present invention means absence of water as an essential element. That is, the "non-aqueous transdermal absorption preparation" of the present invention is an external preparation without water as an element, wherein water normally attached to or stored in a substance or solvent is not considered. For example, among transdermal absorption preparations, poultice containing water as an element is not a non-aqueous transdermal absorption preparation but tapes are.

The "ester solvent" in the present invention means, for example, ester of long chain fatty acid such as oleic acid, caprylic acid, caproic acid, myristic acid, palmitic acid, stearic acid and the like and monovalent aliphatic alcohol (for example, myristic acid esters such as isopropyl myristate, ethyl myristate and the like, palmitic acid esters such as isopropyl palmitate, ethyl palmitate and the like, stearic acid esters such as isopropyl stearate and the like, oleic acid esters such as decyl oleate and the like), medium-chain triglyceride such as caprylic acid triglyceride, caproic acid triglyceride, peanut oil, olive oil, castor oil, cacao oil, hydrogenated fats and oils (e.g., hydrogenated castor oil etc.) and the like, ester of polyvalent carboxylic acid such as adipic acid, sebacic acid and the like and monovalent aliphatic alcohol (e.g., sebacic acid esters such as diethyl sebacate, diisopropyl sebacate and the like, adipic acid esters such as diethyl adipate, diisopropyl adipate and the like), carbonic acid esters such as propylene carbonate etc. and the like.

Preferred are, for example, myristic acid esters such as isopropyl myristate, ethyl myristate and the like, medium-chain triglyceride such as caprylic acid triglyceride, caproic acid triglyceride, peanut oil, olive oil, castor oil, cacao oil, hydrogenated fats and oils (e.g., hydrogenated castor oil etc.) and the like, sebacic acid esters such as diethyl sebacate, diisopropyl sebacate and the like, and propylene carbonate. More preferred are, for example, isopropyl myristate, medium-chain triglyceride, diethyl sebacate, and propylene carbonate.

The "alcohol solvent" in the present invention means, for example, higher alcohols such as benzyl alcohol, lauryl alcohol, myristyl alcohol, cetyl alcohol, stearyl alcohol, cetostearyl alcohol, 2-octyldodecanol and the like, lower alcohols such as ethanol, 2-propanol, 1-propanol and the like, polyvalent alcohols such as ethylene glycol, glycerol, propylene glycol, 1,3-butanediol, polyethylene glycol etc. and the like.

Preferred are, for example, lower alcohols such as ethanol, 2-propanol, 1-propanol and the like, polyvalent alcohols such as ethylene glycol, glycerol, propylene glycol, 1,3-butanediol, polyethylene glycol etc. and the like. More preferred are, for example, 2-propanol, ethylene glycol, polyethylene glycol, propylene glycol, and 1,3-butanediol.

The "amide solvents" in the present invention means, for example, N-methyl-2-pyrrolidone, 1,3-dimethyl-2-imidazolidinone, 2-pyrrolidone, ε-caprolactam, formamide, N-methylformamide, N,N-dimethylformamide, acetamide, N-methylacetamide, N,N-dimethylacetamide, N-methylpropaneamide, hexamethylphosphoric triamide and the like.

Preferred are, for example, N-methyl-2-pyrrolidone, N,N-dimethylformamide, N,N-dimethylacetamide and the like. More preferred is, for example, N-methyl-2-pyrrolidone.

In the present invention, a combined use of an ester solvent and an amide solvent from among these solvents is preferable for improving the transdermal absorbability, and particularly, use of an ester solvent and an amide solvent at 1:1-1:4 is preferable for enhancing the transdermal absorbability-improving effect thereof.

The "transdermal absorption promoter" in the present invention means a reagent generally and widely used in the field of patches to promote transdermal absorption of a drug. Examples of thereof include the above-mentioned organic acids, alcohol solvents, ester solvents, amide solvents, as well as essential oils such as menthol, limonene etc., and the like. Furthermore, the same organic acid as that used for an organic acid salt of a basic medicinal ingredient may also be used as a transdermal promoter, or a different organic acid may also be used. In the case of acetate, lactate and the like of a basic medicinal ingredient, for example, the same acetic acid and lactic acid may be added as a transdermal absorption promoter, or oleic acid, levulinic acid, myristic acid, stearic acid, isostearic acid and the like may also be added. Preferred are menthol, N-methyl-2-pyrrolidone, low volatile fatty acids such as lactic acid, oleic acid, levulinic acid and the like.

As a base of a non-aqueous transdermal absorption preparation in the form of a liquid, the above-mentioned alcohol solvents, ester solvents and amide solvents can be preferably used together with general reagents.

For ointment preparations, for example, oils such as petrolatum, cetanol, beeswax, white beeswax, lanolin, purified lanolin, liquid paraffin, paraffin wax, Plastibase containing liquid paraffin and polyethylene, silicone oil, medium-chain triglyceride, squalene, microcrystalline wax, whale wax etc. and the like can be mentioned.

For plasters (tapes), examples of the elastomer include rubbers such as natural rubber, isoprene rubber, polyisobutylene, styrene-isoprene-styrene block copolymer, styrene-butadiene-styrene block copolymer, styrene-ethylene-butylene-styrene block copolymer, (meth)acrylic acid alkyl ester (co)polymer, polybutene, liquid polyisoprene and the like. Examples of the tackifier include polyterpene resin, polyolefin resin, polystyrene resin, hydrogenated petroleum resin, hydrogenated rosin and the like. Examples of the softening agent include petroleum softening agents such as process oil, low molecular weight polybutene and the like, fatty acid softening agents such as palm oil, castor oil and the like, purified lanolin and the like. As other components, for example, fillers and antioxidants such as zinc oxide, titanium oxide, calcium carbonate, silicic acids and the like can be added as necessary.

The "good transdermal absorbability" in the present invention means that the transdermal absorption preparation of the present invention is superior in the transdermal absorbability (skin permeability) to transdermal absorption preparations containing aripiprazole in a free form and without coexistence of an organic acid. Among the same transdermal absorption preparation compositions, therefore, a transdermal absorption preparation containing a fatty acid salt, which is superior in the transdermal absorbability (skin permeability) to a free form, corresponds to the present invention.

As a surfactant that can be added to a transdermal absorption preparation, a known surfactant can be used as appropriate where necessary.

Examples of the suspending agent or thickener that can be added to a transdermal absorption preparation include polysaccharides such as gum arabic, tragacanth, pullulan, locust bean gum, tamarind gum, pectin, xanthan gum, guar gum, carageenan and the like, methylcellulose, carmellose, carmellose sodium, polyvinyl alcohol, polyvinylpyrrolidone, acrylic acid copolymer, carboxyvinylpolymer, colloidal microcrystalline cellulose and the like.

As the inorganic particles that can be added to a transdermal absorption preparation, for example, talc, silicic anhydride, calcium carbonate, magnesium carbonate, colloidal silica, bentonite and the like can be used. Addition of these enables control of tactile sensation on the skin by the preparation.

As a stabilizer that can be added to a transdermal absorption preparation, for example, preservative, antioxidant and the like can be used. Examples of the aforementioned preservative include p-hydroxybenzoic acid esters such as methylparaben, propylparaben and the like, alcohols such as chlorobutanol, benzyl alcohol, phenylethyl alcohol and the like, thimerosal, acetic anhydride, sorbic acid and the like. Examples of the aforementioned antioxidant include sodium bisulfite, L-ascorbic acid, sodium ascorbate, butylhydroxyanisole, dibutylhydroxytoluene, propyl gallate, tocopherol acetate, dl-α-tocopherol and the like.

In addition to these additives, a pharmaceutical product containing other drug can also be added as long as the action effect of the transdermal absorption preparation of the present invention is not prevented.

The additives exemplified above are appropriately selected according to the dosage form of the transdermal absorption preparation of the present invention. In addition, the amount thereof to be added is also selected as appropriate from the range generally used for each dosage form.

Second Embodiment of the Present Invention

The second embodiment of the present invention is an invention relating to a production method of a transdermal absorption preparation with good transdermal absorbability, comprising forming an organic acid salt of aripiprazole (including equilibrium mixture) to be contained in the preparation system.

The production method of the present invention permits utilization of known conventional means as appropriate, and is particularly a production method of a transdermal absorption preparation, comprising forming an organic acid salt of aripiprazole to be contained in the preparation system by the following steps.

A production method of a non-aqueous transdermal absorption preparation with good transdermal absorbability, comprising a) forming an organic acid salt of aripiprazole by using aromatic carboxylic acid or aliphatic carboxylic acid as an organic acid, and adding a 0.5- to 5-fold molar amount of the organic acid to aripiprazole as 1, b) diluting the above-mentioned organic acid salt with at least one selected from an ester solvent, an alcohol solvent and an amide solvent, and c) dispersing the above-mentioned diluted solution in a base of an external preparation.

The definition of the above-mentioned terms and other additives are the same as those described for the aforementioned first embodiment.

The present invention is explained in more detail in the following by referring to Examples, which are not to be construed as limitative. The present invention can also be changed and practiced as appropriate, all of which changes are encompassed in the technical scope of the present invention.

EXAMPLES

Example 1

Synthesis of an Organic Acid Salt of Aripiprazole

Aripiprazole (200 mg, 0.446 mM) and an equimolar amount of an organic acid described in the following Table 1 were weighed, and dissolved in tetrahydrofuran (1 mL). Tetrahydrofuran was evaporated under reduced pressure to give an organic acid salt of aripiprazole as crystals. Furthermore, the crystals were recrystallized from ethyl acetate or THF. The melting point of the obtained crystals was measured by a micro melting point measuring instrument.

In infrared absorption spectrum, the absorption band near 1700-1720 cm-1 of the starting monocarboxylic acid disappeared, and the absorption of carboxyl ion considered to have been produced overlapped with IR absorption of aripiprazole and could not be identified.

TABLE 1

| organic acid | melting point (° C.) | IR (Nujol method) cm$^{-1}$ |
|---|---|---|
| aripiprazole (free form) | 137-138 | 1670 (lactamcarbonyl) |
| monocarboxylic acid | | |
| glycolic acid | 127-128 | 1660 (lactamcarbonyl), near 3500 (OH) |
| DL-mandelic acid | 161-162 | 1675 (lactamcarbonyl), 3340 (OH) |
| dicarboxylic acid | | |
| adipic acid | 116 | 1670 (lactamcarbonyl), near 1710 (COOH) |
| sebacic acid | 108-109 | 1650 (lactamcarbonyl), 1720 (COOH) |

Since the pKa value of aripiprazole is 7.6 and almost neutral, the equilibrium of salt tends to easily move toward dissociation into acid and base. In addition, aripiprazole has good crystallinity, and its free form tends to easily precipitate as crystals. Therefore, use of substituted aliphatic carboxylic acid containing one or more hydroxyl groups and/or ketone groups as substituent(s) is considered to be appropriate for forming a salt to enhance solubility in a solvent.

Example 2

Liquid Containing Aliphatic Carboxylic Acid Salt of Aripiprazole Formed Therein

Aripiprazole (20 mg, 0.045 mM) and each equimolar amount of an organic acid shown in the following Table 2 were weighed in a sample container. A solvent with the solvent composition in a mass ratio of diethyl sebacate:medium-chain triglyceride:N-methyl-2-pyrrolidone:propylene glycol (65:20:7.5:7.5) was added. The total amount was adjusted to 1000 mg to give a liquid containing an aripiprazole.organic acid salt (containing 2 w/w % aripiprazole) in the system. The transdermal absorbability was evaluated using the skin of a rat and a Franz diffusion cell and according to the method of Experimental Example 1.

Figure 1:
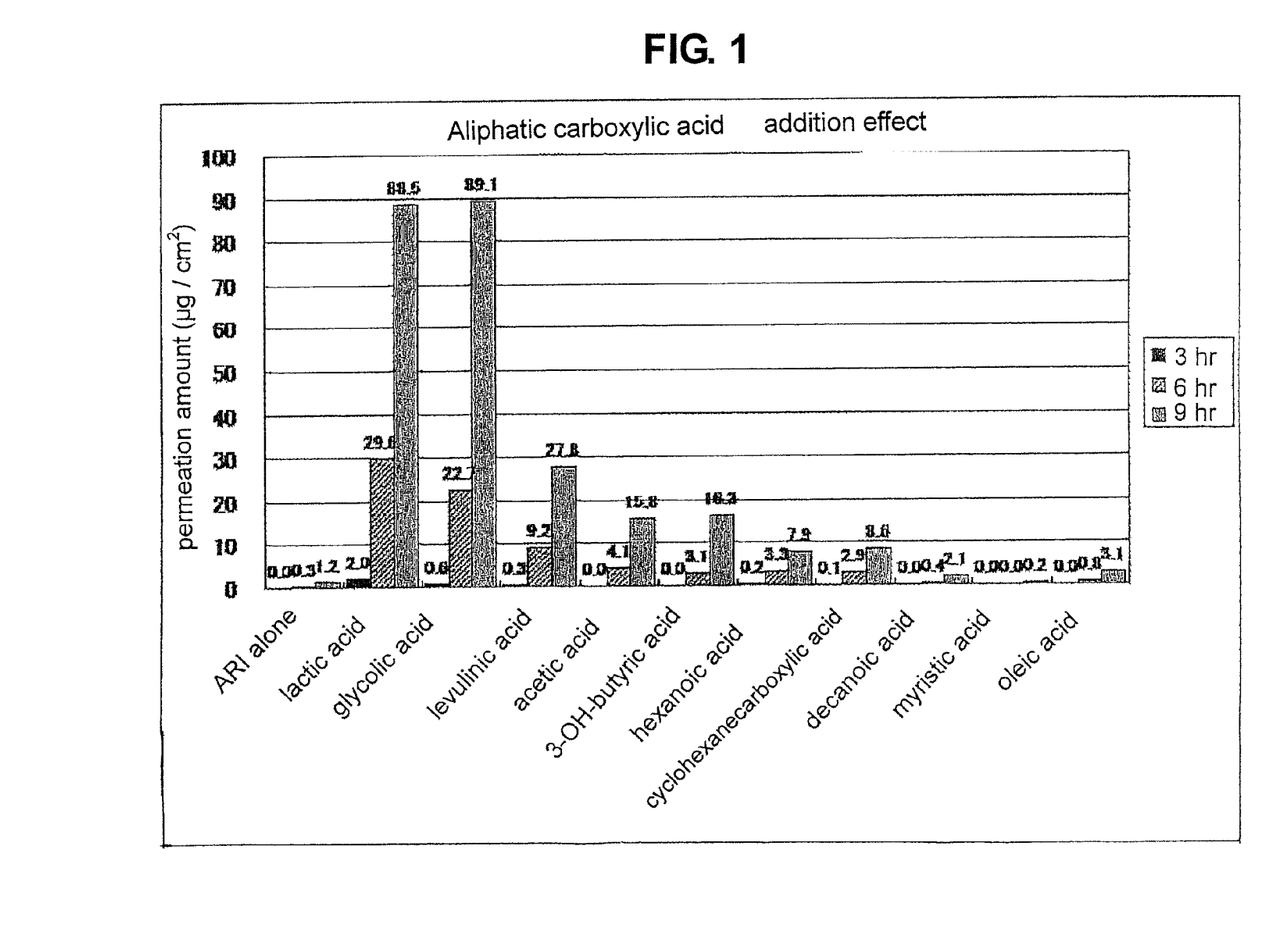
FIG. 1 shows the results of an in vitro transdermal absorbability test using a liquid containing equimolar amounts of aripiprazole and aliphatic carboxylic acid.
Figure 2:
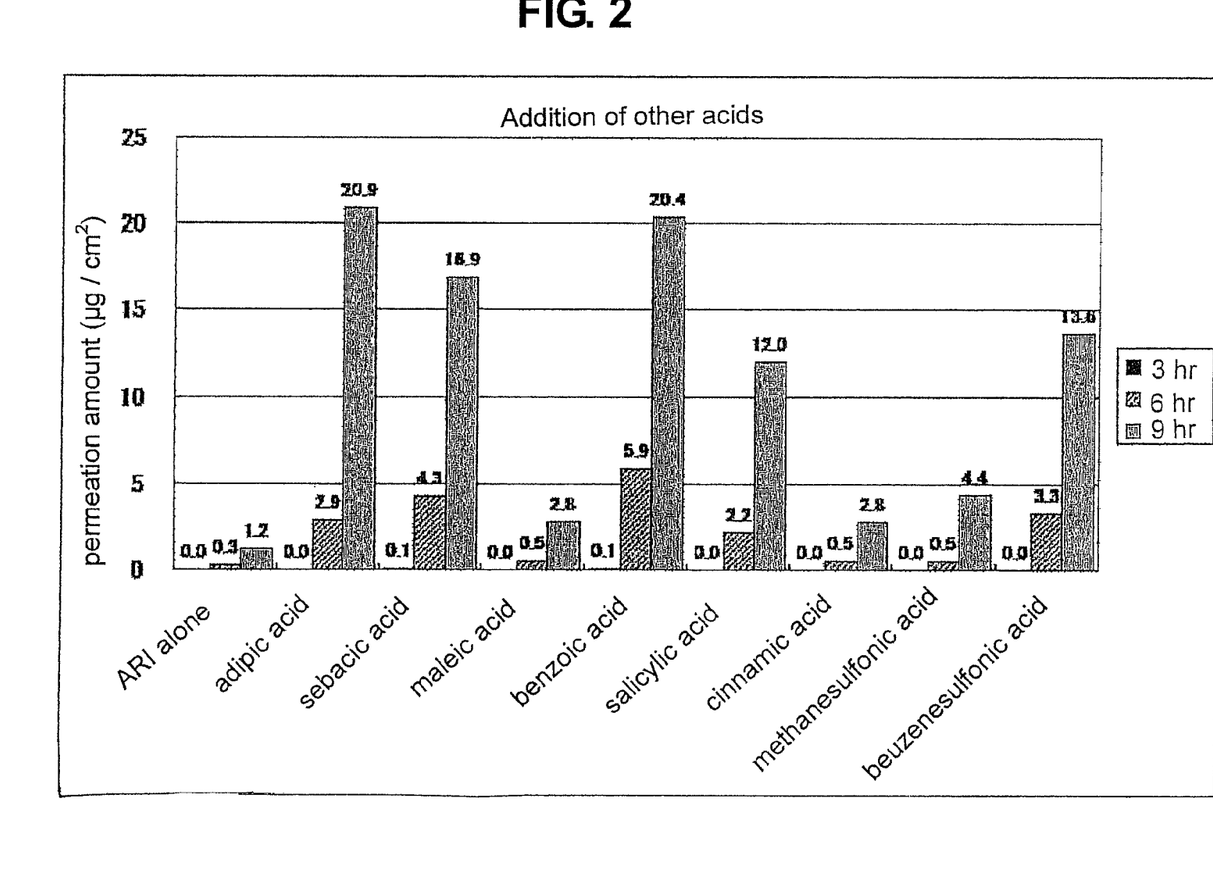
FIG. 2 shows the results of an in vitro transdermal absorbability test using a liquid containing equimolar amounts of aripiprazole, aromatic carboxylic acid and sulfonic acid.

The results are shown in Table 2, FIG. 1 and FIG. 2.

TABLE 2

| organic acid (equimolar addition) | logP calculated value of organic acid | permeation amount (μg/cm$^2$) in 9 hr |
|---|---|---|
| aripiprazole (free form) | 4.6 | 1.2 |
| monocarboxylic acid | | |
| oleic acid | 6.5 | 3.1 |
| myristic acid | 5.3 | 0.2 |
| decanoic acid | 4.1 | 2.1 |
| cyclohexanecarboxylic acid | 1.9 | 8.6 |
| hexanoic acid | 1.9 | 7.9 |
| acetic acid | −0.2 | 15.8 |
| levulinic acid | −0.5 | 27.8 |
| 3-hydroxybutyric acid | −0.6 | 16.3 |
| lactic acid | −0.7 | 88.5 |
| glycolic acid | −1.1 | 89.1 |

TABLE 2-continued

| organic acid (equimolar addition) | logP calculated value of organic acid | permeation amount (μg/cm$^2$) in 9 hr |
|---|---|---|
| dicarboxylic acid | | |
| sebacic acid | 2.1 | 16.9 |
| adipic acid | 0.1 | 20.9 |
| maleic acid | −0.3 | 2.8 |

[Note]
As the logP calculated value of organic acid, the PubChem value (revised on February, 2009) was used.

Since aripiprazole is highly lipophilic (logP: 4.6), when monocarboxylic acid was used as a usable organic acid, carboxylic acid having lower lipophilicity than hexanoic acid (logP: 1.9) was found to show good transdermal absorbability (skin permeability). Furthermore, when dicarboxylic acid was used, dicarboxylic acid having lipophilicity not higher than that of sebacic acid (logP: 2.1) and higher than that of maleic acid (logP: −0.3) showed good transdermal absorbability. Thus, it has been clarified that the optimal range of logP of organic acid varies between monocarboxylic acid and dicarboxylic acid.

Example 3

Effect of Addition of Lactic Acid to Aripiprazole

To a 2 w/w % aripiprazole solution of Example 2 was added lactic acid in the molar amount described in Table 3 to give a liquid containing lactate of aripiprazole. The liquids were subjected to Franz diffusion cell according to the method of Experimental Example 1 and transdermal absorbability was evaluated.

The results are shown in the following Table 3 and FIG. 3.

TABLE 3

| lactic acid addition molar ratio (-fold molar amount) | 3 hr later (μg/cm$^2$) | 6 hr later (μg/cm$^2$) | 9 hr later (μg/cm$^2$) |
|---|---|---|---|
| 0 | 0.0 | 0.3 | 1.2 |
| 0.5M | 2.1 | 21.9 | 65.5 |
| 1.0M | 2.0 | 29.6 | 88.5 |
| 2.0M | 2.7 | 41.1 | 116.1 |
| 3.0M | 1.3 | 33.4 | 180.1 |
| 5.0M | 4.4 | 60.6 | 180.7 |

As shown in Table 3 above, the transdermal absorbability of a liquid containing lactate of aripiprazole was found to hit the ceiling when lactic acid was present in not less than 3-fold molar amount relative to aripiprazole. Since the pKa value of aripiprazole is 7.6, a 3-fold molar amount of lactic acid was considered to be necessary for shifting the dissociation equilibrium of acid and base toward salt.

Example 4

Liquid Containing Aromatic Carboxylic Acid Salt and Sulfonate of Aripiprazole

As organic acids having a pKa value lower than that of aliphatic carboxylic acid, and salt dissociation equilibrium tending to shift toward salt formation, aromatic carboxylic acid and sulfonic acid were selected. An organic acid salt of aripiprazole was produced in the same manner as in Example 2. First, the organic acids shown in the following Table 4 were used, each equimolar amount was added and the mixture was stirred to give liquids containing an aripiprazole.organic acid salt containing 2 w/w % aripiprazole in the system.

The transdermal absorbability was evaluated in the same manner as in Example 2.

The results are shown in Table 4 and FIG. 2.

TABLE 4

| organic acid (equimolar addition) | logP calculated value of organic acid | permeation amount (μg/cm²) in 9 hr |
|---|---|---|
| aripiprazole (free form) | 4.6 | 1.2 |
| aromatic carboxylic acid | | |
| salicylic acid | 2.3 | 12.0 |
| cinnamic acid | 2.1 | 2.8 |
| benzoic acid | 1.9 | 20.4 |
| sulfonic acid | | |
| benzenesulfonic acid | 0 | 13.6 |
| methanesulfonic acid | −0.9 | 4.4 |

[Note]
As the logP calculated value of organic acid, the PubChem value was used in the same manner as in Example 2.

Since the acidity of benzenesulfonic acid (pKa: −2.5) and methanesulfonic acid (pKa: −2.0) is high, the dissociation equilibrium of the sulfonate of aripiprazole is considered to be shifted toward salt. However, even when the equilibrium is shifted toward salt, and the concentration of ion pair is high, the transdermal absorbability has not increased much. It has been found that the transdermal absorbability is not good unless the lipophilicity of the ion pair is adequate, even if the concentration of the ion pair (sulfonate) formed in the preparation system is high. These demonstrate that the lipophilicity of the ion pair (organic acid salt) of aripiprazole formed in the preparation greatly contributes to the transdermal absorption of aripiprazole.

Example 5

Influence of Solvent Composition and Aripiprazole Concentration in Liquid Containing Lactate of Aripiprazole To a 2 w/w % aripiprazole solution (solvent composition: diethyl sebacate (hereinafter DES)/medium-chain triglyceride/N-methyl-2-pyrrolidone (hereinafter NMP)/propylene glycol=65/20/7.5/7.5, hereinafter solvent A) of Example 3 was added a 2-fold molar amount of lactic acid to give a liquid containing lactate of aripiprazole. Furthermore, liquids containing aripiprazole, a 2-fold molar amount of lactic acid and a solvent as described in Table 5 were produced. These liquids were subjected to Franz diffusion cell according to the method of Experimental Example 1 and the transdermal absorbability was evaluated.

Figure 4:
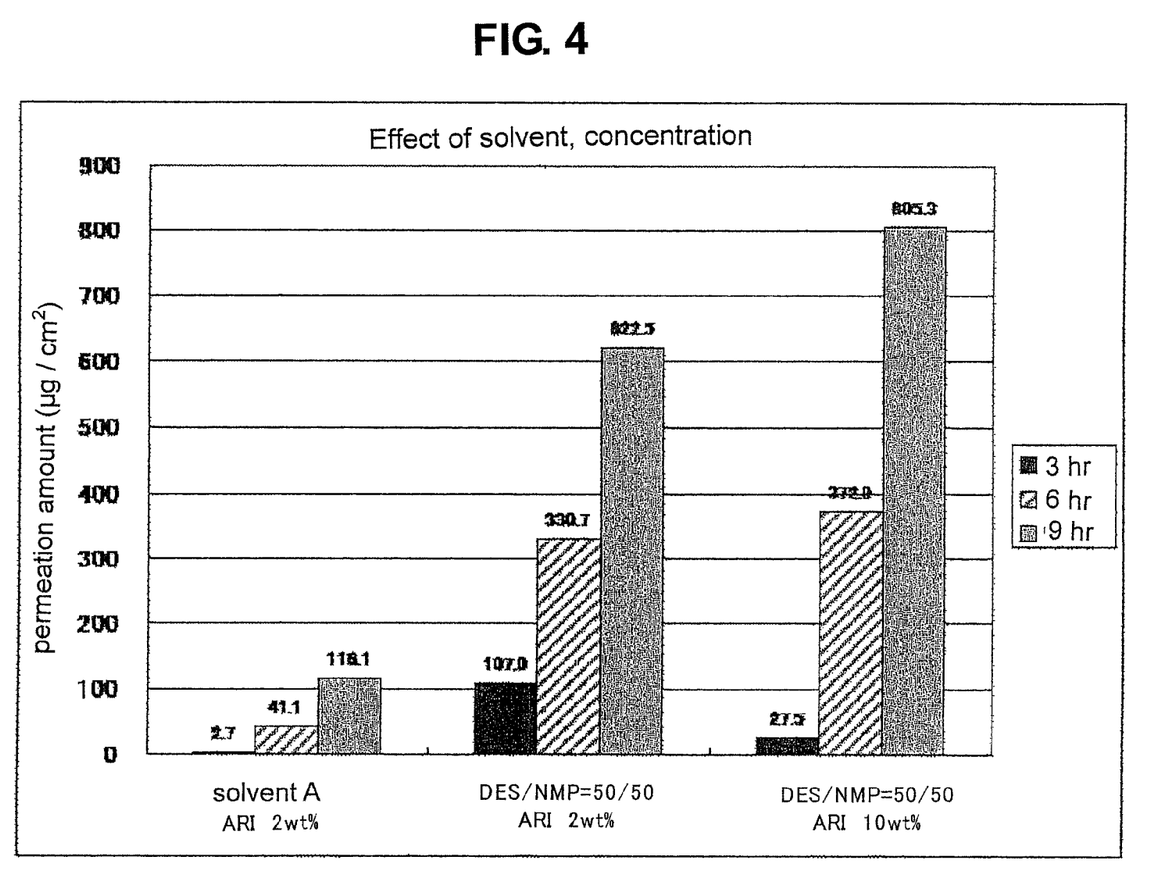
FIG. 4 shows the effect of changes of the solvent composition dissolving aripiprazole on transdermal absorbability of aripiprazole.

The results are shown in the following Table 5 and FIG. 4.

TABLE 5

| | (Example 3 + 2M lactic acid) | No. 1 | No. 2 |
|---|---|---|---|
| aripiprazole (free form) | 2.0 | 2.0 | 10.0 |
| lactic acid | 2-fold molar amount | 2-fold molar amount | 2-fold molar amount |
| solvent | solvent A: about 97.0 | DES/NMP (1:1) about 97.0 | DES/NMP (1:1) about 85.0 |

TABLE 5-continued

| | (Example 3 + 2M lactic acid) | No. 1 | No. 2 |
|---|---|---|---|
| transdermal absorbability (μg/cm²): | | | |
| 3 hr later | 2.7 | 107.0 | 27.5 |
| 6 hr later | 41.1 | 330.7 | 372.9 |
| 9 hr later | 116.1 | 622.5 | 805.3 |

[Note]
DES: diethyl sebacate
NMP: N-methyl-2-pyrrolidone

As shown in the above-mentioned Table 5, the transdermal absorbability of the liquid containing lactate of aripiprazole was shown to drastically increase by changing the solvent composition to fatty acid ester and amide solvent alone (No. 1), and using aripiprazole at a high concentration (No. 2).

Example 6

Effect of Solvent Ratio in Liquid Containing Lactate of Aripiprazole

Liquids with solvent compositions changed as described in Table 6 were produced, based on the liquid of No. 2 (10 w/w % aripiprazole, 2-fold molar amount of lactic acid) in Example 5. These liquids were subjected to Franz diffusion cell according to the method of Experimental Example 1 and the transdermal absorbability was evaluated.

The results are shown in the following Table 6 and FIG. 5.

TABLE 6

| solvent composition DES/NMP | 3 hr later (μg/cm²) | 6 hr later (μg/cm²) | 9 hr later (μg/cm²) |
|---|---|---|---|
| 0/100 | 0.0 | 0.0 | 0.6 |
| 10/90 | 0.2 | 94.6 | 675.2 |
| 20/80 | 8.0 | 326.8 | 706.3 |
| 25/75 | 156.2 | 806.8 | 1679.1 |
| 50/50 | 31.0 | 317.4 | 855.9 |
| 75/25 | 2.0 | 81.4 | 302.4 |
| 100/0 | 0.1 | 2.4 | 8.7 |

[Note]
DES: diethyl sebacate
NMP: N-methyl-2-pyrrolidone

Figure 5:
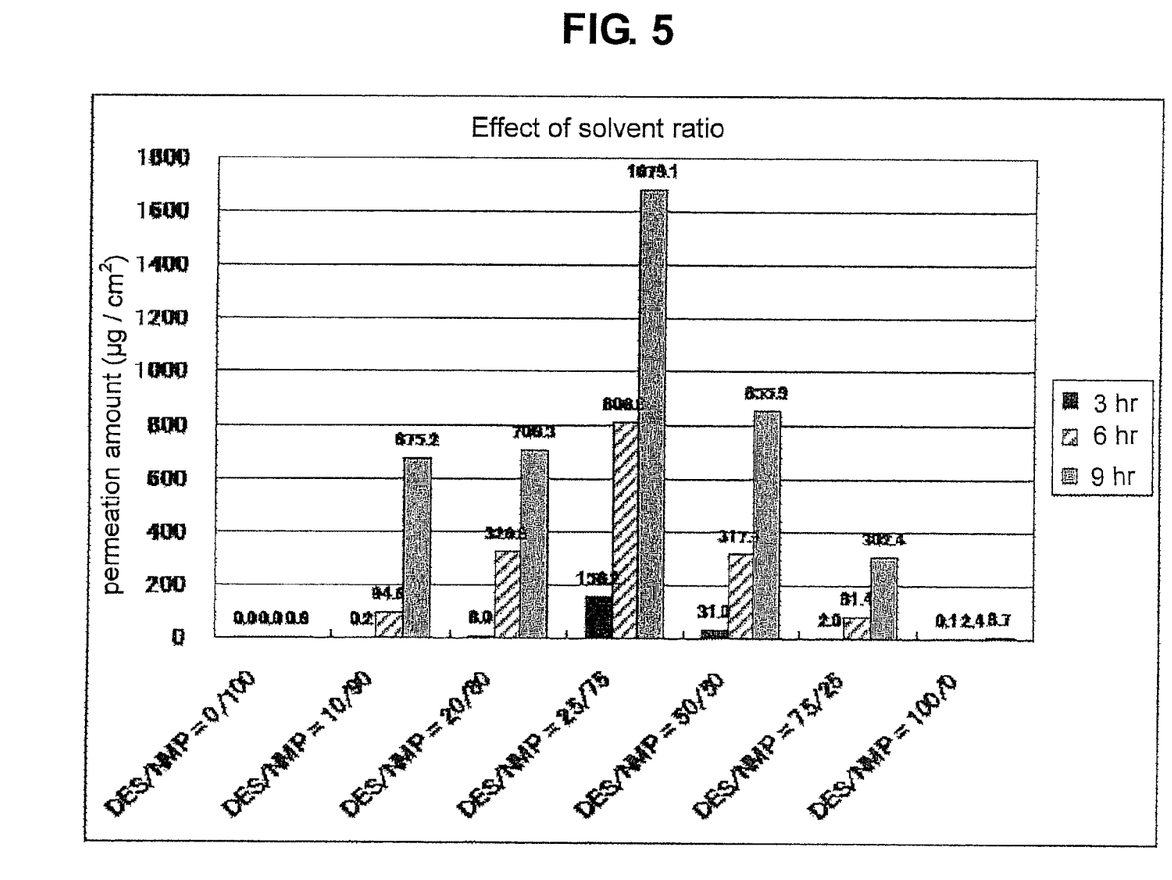
FIG. 5 shows the effect of changes of the solvent composition of diethyl sebacate and N-methyl-2-pyrrolidone on transdermal absorbability of aripiprazole.

As shown in the above-mentioned Table 6, the transdermal absorbability of liquids containing lactate of aripiprazole changed according to the mixing ratio of fatty acid ester and amide solvents in the solvent composition and, as shown in FIG. 5, depicted a bell-shaped curve. It has been found that the transdermal absorbability is improved within the fatty acid ester/amide solvent range of 50/50-20/80. Particularly, the transdermal absorbability was found to reach the maximum when the composition of fatty acid ester/amide solvents is near 25/75.

Experimental Example 1

Evaluation Test of Transdermal Absorbability of Liquid Containing Aripiprazole

For comparison examination of the transdermal absorbability of the transdermal absorption preparations containing an aripiprazole organic acid salt formed in the preparation system, the liquids of Examples 2-6 (each 100 μL) were separated, and applied to a transdermal absorbability evaluation test using Franz diffusion cell (permeation area: 1 cm², receptor liquid volume: 8 mL) at test temperature 32° C., as shown below.

(1) rat skin: 5-week-old Wistar rat (male) isolated skin of abdomen (2) receptor solution: saline:ethanol (10:1)

(3) concentration measurement of permeated drug: HPLC-ES method (230 nm)

A commercially available rat abdominal frozen skin (5-week-old Wistar rat) was sandwiched between vertical diffusion cells (effective diffusion area: 1 cm$^2$), and each sample described in Table 5 was applied to the stratum corneum layer side and a physiological saline/ethanol (10:1) solution was applied to the dermic layer side. At 3 hr, 6 hr and 9 hr from the start of the experiment, physiological saline (100 µL) was sampled, the concentration of the drug that permeated through the skin was measured by HPLC, and the cumulative permeation amount of the drug at each time point was measured. As a result, the transdermal absorbability of organic acid salts of aripiprazole could be evaluated as shown in FIGS. 1-5.

INDUSTRIAL APPLICABILITY

Using the production method of the transdermal absorption preparation of the present invention, a transdermal absorption preparation superior in the transdermal absorbability of aripiprazole can be produced. To be specific, an appropriate organic acid (organic acid with low lipophilicity) is selected based on the combination of the lipophilicity of medicinal ingredient (logP: 4.6) and the lipophilicity (logP) of organic acid, and an organic acid salt of aripiprazole with good transdermal absorbability can be formed in the preparation system. That is, by appropriately combining organic acids having lipophilicity within the range of −1.5 to 2, preferably −1.5 to 0, an organic acid salt of aripiprazole with good transdermal absorbability can be produced in the preparation system.

Furthermore, an external preparation composition showing desired transdermal absorbability can be produced by appropriately selecting and using an organic solvent, a transdermal absorption promoter, a surfactant and the like with the organic acid salt of aripiprazole or an equilibrium mixture thereof obtained in the present invention to dissolve or disperse aripiprazole in a base of the external preparation composition. Thus, the present invention provides a transdermal absorption preparation of aripiprazole, which shows good transdermal absorbability.

The invention claimed is:

1. A transdermal absorption preparation comprising a single active agent, an ester solvent, and an amide solvent,
   wherein the single active agent is a lactic acid salt of aripiprazole,
   wherein the molar ratio of the lactic acid to aripiprazole is from 0.5:1 to 3:1,
   wherein the weight ratio of the ester solvent to the amide solvent is from 1:1 to 1:4;
   wherein the amide solvent is selected from the group consisting of N,N-dimethylformamide, N,N-dimethylacetamide, N-methyl-2-pyrrolidone, and combinations thereof, and
   wherein the ester solvent is selected from the group consisting of isopropyl myristate, diethyl sebacate, medium-chain triglyceride, propylene carbonate, and combinations thereof.

2. The transdermal absorption preparation according to claim 1, further comprising an alcohol solvent that is selected from the group consisting of propylene glycol, 2-propanol, 1,3-butanediol, ethylene glycol, polyethylene glycol, and combinations thereof.

3. The transdermal absorption preparation according to claim 1, wherein the molar ratio of lactic acid and aripiprazole is 1:1.

4. The transdermal absorption preparation according to claim 1, which is a non-aqueous transdermal absorption preparation.

5. A method of producing a transdermal absorption preparation comprising a single active agent, ester solvent, and an amide solvent, which comprises the steps:
   (a) forming a lactic acid salt of aripiprazole by adding lactic acid in a molar ratio of lactic acid to aripiprazole of from 0.5:1 to 3:1,
   (b) diluting the above-mentioned lactic acid salt with the ester solvent and the amide solvent in a weight ratio of ester solvent to amide solvent of from 1:1 to 1:4,
   wherein
   the transdermal absorption preparation comprises a single active agent,
   the single active agent is a lactic acid salt of aripiprazole,
   the amide solvent is selected from the group consisting of N,N-dimethylformamide, N,N-dimethylacetamide, N-methyl-2-pyrrolidone, and combinations thereof, and
   the ester solvent is selected from the group consisting of isopropyl myristate, diethyl sebacate, medium-chain triglyceride, propylene carbonate, and combinations thereof,
   and
   (c) dispersing the above-mentioned diluted solution in a base of an external preparation.

6. The production method according to claim 5, wherein step (b) further utilizes an alcohol solvent that is selected from the group consisting of isopropanol, ethylene glycol, propylene glycol, 1,3-butanediol, and combinations thereof.

7. The production method according to claim 5, wherein the molar ratio of lactic acid and aripiprazole in step (a) is 1:1.

8. The production method according to claim 5, wherein the transdermal absorption preparation is a non-aqueous transdermal absorption preparation.

9. The production method according to claim 8, wherein the non-aqueous transdermal absorption preparation is a tape preparation.

10. The transdermal absorption preparation according to claim 4, wherein the non-aqueous transdermal absorption preparation is a tape preparation.

* * * * *